(12) United States Patent
Gwon

(10) Patent No.: US 7,278,990 B2
(45) Date of Patent: Oct. 9, 2007

(54) CONTROLLED OCULAR LENS REGENERATION

(76) Inventor: Arlene E. Gwon, 8 Trafalgar, Newport Beach, CA (US) 92660

(*) Notice: Subject to any disclaimer, the term of this patent is extended or adjusted under 35 U.S.C. 154(b) by 74 days.

(21) Appl. No.: 11/223,673

(22) Filed: Sep. 9, 2005

(65) Prior Publication Data

US 2006/0084950 A1 Apr. 20, 2006

Related U.S. Application Data

(63) Continuation of application No. 10/894,140, filed on Jul. 19, 2004, now Pat. No. 6,945,971.

(51) Int. Cl.
*A61F 9/007* (2006.01)
(52) U.S. Cl. .................. 606/5; 128/898; 606/4
(58) Field of Classification Search ........... 128/898; 606/4–6
See application file for complete search history.

(56) References Cited

U.S. PATENT DOCUMENTS

| | | | |
|---|---|---|---|
| 5,620,013 A * | 4/1997 | Bretton | 128/898 |
| 6,089,234 A * | 7/2000 | Bretton | 128/898 |
| 6,945,971 B1 * | 9/2005 | Gwon | 606/5 |
| 6,949,093 B1 * | 9/2005 | Peyman | 606/5 |
| 7,001,374 B2 * | 2/2006 | Peyman | 606/5 |
| 2001/0034516 A1 * | 10/2001 | Peyman | 606/5 |
| 2004/0049174 A1 * | 3/2004 | Peyman | 606/5 |
| 2005/0283211 A1 * | 12/2005 | McDaniel | 607/86 |
| 2006/0084950 A1 * | 4/2006 | Gwon | 606/4 |

* cited by examiner

*Primary Examiner*—Henry M Johnson, III
(74) *Attorney, Agent, or Firm*—Walter A. Hackler

(57) ABSTRACT

A method for treating an ocular condition in a mammal includes removing an original lens to leave an empty lens capsule, filling the empty lens capsule with a gas to maintain capsule tension and prevent folding of the empty lens capsule, disposing a substance into said empty lens capsule that providing an internal scaffold for proliferation and differentiation of lens fibers; and selectively removing said substance by laser photoablation.

14 Claims, 5 Drawing Sheets

CONTROLLED OCULAR LENS REGENERATION

The present application is a continuation of U.S. Ser. No. 10/894,140 filed Jul. 19, 2004 now U.S. Pat. No. 6,945,971 and said application is incorporated herewith in its entirety.

The present invention generally relates to the regeneration of ocular tissue and more particularly relates to the treatment of conditions, as for example, lenticular disorders and controlled regeneration of lens tissue.

Regeneration and repair are the fundamental features of the healing response. The ability to regenerate (i.e., to replace damaged tissue with healthy cells of similar type) varies among tissues and may be seen in the corneal epithelium and conjunctiva. While the healing response in and around the eye occurs primarily because of tissue repair mechanisms (i.e., damaged tissue is replaced by a newly generated fibrous connective tissue) rather than regeneration, there is substantial data suggesting that regeneration of the natural lens is possible. Ideally, the regenerated lens, with or without a suitably flexible and biocompatible polymeric lens, would have all the properties of the natural lens including clarity, protein content, histology, focusing power and accommodative ability. Optimally, corrective powers could optionally be included, later added, in combination with related mechanisms imparting ameliorative visual acuity enhancements.

Extracapsular cataract extraction with implantation of an intraocular lens (IOL) is currently the most common method for the treatment of cataracts. This procedure is less than ideal because the current synthetic intraocular lenses are unable to accommodate appreciably, and secondary opacification of the posterior capsule is a common occurrence. While intraocular implantation of multifocal or accommodating intraocular lenses (IOLs) attempt to address the need for far and near vision in the cataract patient, they are complicated by the development of posterior capsule opacification and visual dysphotopsias. Posterior capsule opacification (PCO) occurs secondary to anterior lens epithelial cell migration and myoblastic transformation and contributes to wrinkling of the posterior capsule and visual distortion.

Ideally, if a regenerated natural lens could replace a suitable biodegradable or ablatable material, the reformed lens would have the same or similar natural focusing power as the normal young lens and be able to accommodate. Alternatively, if naturally regenerating lens epithelial cells could be directed or controlled to grow in a regularly organized pattern around a suitable scaffold, the resultant bilenticular system may be able to accommodate. Other and further corrections and enhancements would be within the purview of artisans, and are within the scope of the instant teachings.

Hyaluronic acid has been shown to be beneficial in wound healing in various body tissues. Hyaluronic acid in the form of Healon® (available from PHARMACIA AB, Gronigen, NL) has been used to fill the lens capsule bag following phacoemulsification (i.e., a cataract surgical procedure which uses an ultrasonic vibration to shatter and break up a cataract for removal) and irrigation/aspiration of both the natural and cataractous lens and sealing of the anterior capsule in the rabbit. However, the Healon® normally is resorbed by about one week postoperatively when the regenerating lens cells are in various stages of development. Additionally, over time the regenerated lens has had an abnormal nucleus in the form of a star-shaped opacity as the earliest lens fibers regenerated at different rates.

There is therefore a need in the art for a regenerated lens (with or without a suitably flexible and biocompatible polymeric lens) which would have all the properties of the natural lens including clarity, protein content, histology, focusing power, accommodative ability, configuration, shape, and structure. There is a further need in the art for the controlled or managed regeneration of a clear natural lens with or without a biocompatible polymer lens in which the former may be applicable to treatment of cataract in the pediatric population and the latter suitable for adult cataract, offering true accommodation and correction of presbyopia. There is additionally a need to improve lens cell proliferation and differentiation following phacoemulsification and irrigation/aspiration. Furthermore, there is a need in the art to treat ocular disease and/or correct vision impairments without its associated complications, as for example, posterior capsule opacification.

SUMMARY OF THE INVENTION

A method for treating an ocular condition in a mammal, as well as for controlling the shape of regenerating lens tissue that generally includes the removal of an original lens to leave an empty lens capsule and thereafter disposing a scaffold within the empty lens capsule. The scaffold enables proliferation and differentiation of lens fibers, or tissue, thereafter the scaffold is selectively removed by laser photoablation.

More particularly, in accordance with the present invention, a portion of the proliferated lens fibers, or tissue, may be removed by laser photoablation in order to control the shape and size of the proliferated lens fiber or tissue.

More particularly, the photoablation may include focusing a laser on the lens capsule of the focal point below an anterior surface of the lens capsule, pulsing the laser at the focal point, and moving the focal point toward the anterior surface of the lens capsule while pulsing the laser to ablate at least a portion of the scaffold and/or proliferated lens fiber or tissue.

Still more particularly, disposing a scaffold in the empty lens capsule may include disposing a hyaluronic acid composition in the lens capsule and a composition may be selected from the group consisting of Restylane®, Perlan®, and combinations thereof.

A collagen, or collagen-based product, may be injected into the lens capsule with the collagen-based product being selected from the group consisting of Zyderm®, Resoplast®, Dermalogen®, and Allooderm®.

Preferably, the scaffold is formulated to dissolve substantially entirely by the end of eight weeks after disposition into the lens capsule.

In this manner, the method in accordance to the present invention provides for restoring ocular lenses in mammals.

DETAILED DESCRIPTION

The present invention is based on the concept that the natural lens is capable of controlled or enhanced organic cellular or biological regeneration following endocapsular lens and/or cataract extraction. In various embodiments, the present invention provides methods to produce a regenerated lens with properties similar to that of the natural lens, including clarity, protein content, histology, focusing power and accommodative ability.

In one embodiment, the natural regenerating lens tissue may be directed to grow in a more natural or regular pattern around a suitably flexible and biocompatible polymeric lens. The resultant bilenticular system of this embodiment has clarity, focusing power, and accommodative ability similar to the natural lens. Yet, in another aspect, lenticular tissue may be controlled or engineered using focal laser photophacocoagulation to remove excess viscoelastic substances and/or to modify structure and clarity of the regenerated lens and/or bilenticular lens.

Figure 1:
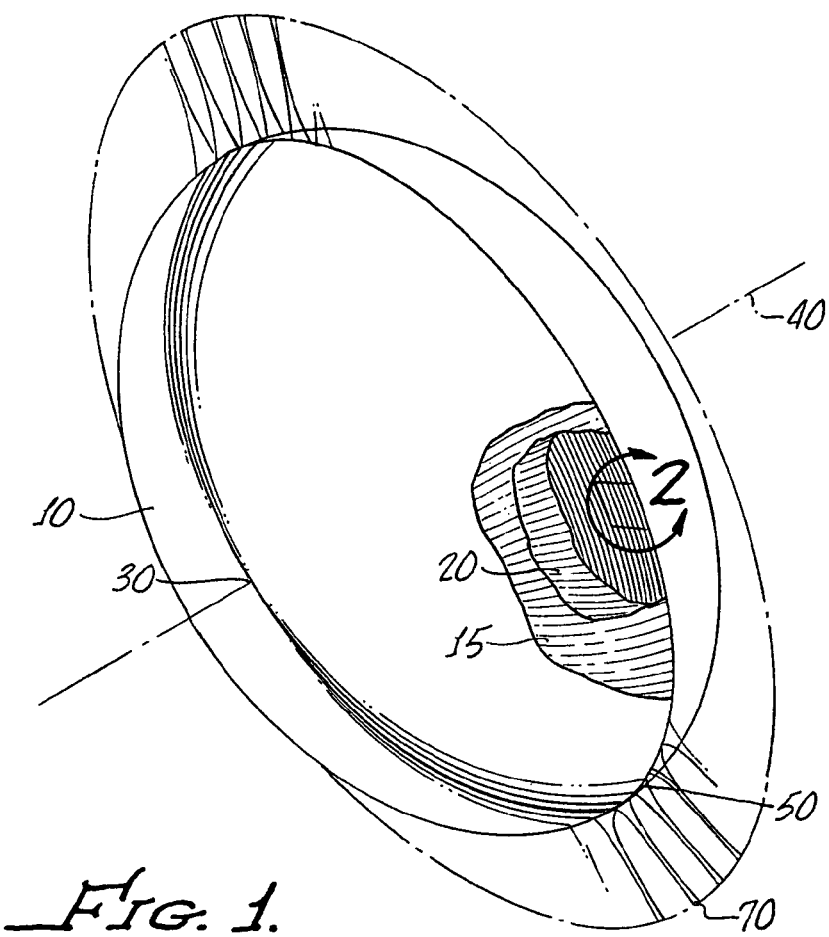
FIG. 1 (prior art) illustrates the gross morphology of the lens fibers generated in the cortex in accordance with an embodiment of the present invention.
Figure 2:
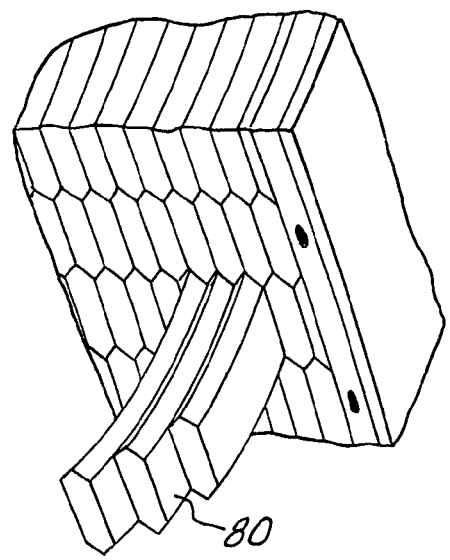
FIG. 2 (prior art) illustrates a lens fiber depicted in FIG. 1 in accordance with an embodiment of the present invention.

FIG. 1 depicts the human lens and the gross morphology of the lens fibers generated in the cortex 15. FIG. 1 also depicts the capsule 10, nucleus 20, zonule 70, the anterior pole 30, equator 50, and optical axis 40 of the lens. These regenerated lens fibers originate as epithelial cells and elongate into ribbon-like nucleus-free lens components. The cross sections of these lens components are hexagonal in shape. FIG. 2 depicts a closer view of a lens fiber 80, which has a hexagonal cross-section.

Since the first description by Cocteau and Leroy D'Etoille (1827) the residual lens epithelial cells that contribute to secondary cataract formation have been shown to regenerate and differentiate more normally if the integrity of the lens capsule is restored following endocapsular lens extraction in rabbits. Lens fiber differentiation has been shown to follow a process similar to embryological development with cellular proliferation along the anterior and posterior capsule, followed by elongation of the posterior epithelial cells, anterior migration of fiber nuclei and subsequent differentiation at the equatorial zone.

The regenerated lenses have been shown to contain all the major crystallins—alpha, beta and gamma—in proportions similar to fetal or normal lenses. In these earlier studies, regeneration is noted as early as 2-3 weeks postoperative, and capsule bag filling with regenerated lens tissue is seen at 7-10 weeks postoperative (A. Gwon et al., "Restoration of Lens Capsule Integrity Enhances Lens Regeneration in New Zealand Albino Rabbits," ARVO, Sarasota, Fla. (May 1992)). In addition, lens regeneration has been shown to occur after endocapsular extraction of a concanavalin A-induced cataract.

As discussed herein, restoring the lens capsule integrity by insertion of a collagen patch at the time of surgery has enhanced the growth rate and shape/structure of the regenerated lenses in both rabbits and cats (Example 2). The regenerated lenses were spherical. Thus, the regenerated lenses had a normal cortex with good structure and clarity. The nucleus contained a star-shaped opacity related to the irregular growth pattern and misalignment of the earliest lens fibers. In previous studies, various viscoelastic agents had been used to fill the capsule bag following lens/cataract removal. Hyaluronic acid in the form of Healon® has provided some success to date. However, hyaluronic acid in the commercial available form of Healon® biodegrades too fast (hyaluronic acid is resorbed by about one week postoperatively), and the regenerated lens has an abnormal nucleus in the form of a star-shaped opacity as the earliest lens fibers regenerate at different rates.

More recently, as the inventor has demonstrated, high viscosity hyaluronic acid provided an internal scaffold for the proliferation and differentiation of regenerating lens fibers following endocapsular lens extraction in Dutch Belt pigmented rabbits with good early lens fiber alignment and differentiation. The scaffold may be biodegradable or non-biodegradable. The regenerated lenses have a normal spherical shape and the lens structure is clear with normal lens fiber alignment around the spherical residual viscoelastic material. In addition, in the one eye treated with focal photocoagulation with a Q-switched neodymium: YAG (Nd: Yag) laser, the inventor has demonstrated that partial clearing of the hyaluronic acid was attained. Thus, the regeneration of tissue is controlled. Further, control is accomplished through the laser ablation of regenerating cells in order to conform the lens shape to a desired configuration. On histological examination, the lens structure was normal with a monolayer of anterior lens epithelium, lens differentiation occurring at the equatorial region and normal lens fiber structure. Centrally, the retained hyaluronic acid appears as an elliptical homogenous bluish mass.

The concept of creating a bilenticular system by implantation of a suitably flexible polymeric lens compatible with the naturally regenerating lens tissue was previously suggested by studies in which Acuvue® contact lenses (etafilcon A, 58% $H_2O$; available from Johnson & Johnson Vision Care, Inc., Jacksonville, Fla.) were modified for intralenticular implantation in the rabbit eye. While normal regeneration was noted in one eye, the results were inconsistent and the nucleus of most regenerated lenses contained a star-shaped opacity related to the irregular growth pattern and misalignment of the earliest lens fibers.

The mammalian lens, like other ectodermal tissues, can regenerate itself given the proper environment (A. Gwon et al., "Induction of de novo Synthesis of Crystalline Lenses in Aphakic Rabbits," *Exp Eye Res.*, 49:913-926 (1989)). Since 1781, researchers have known that the crystalline lens of amphibians can be regenerated after partial removal of the eye contents, or lensectomy. The lens is regenerated either from the corneal epithelium or the iris epithelium. Regeneration depends upon factors relating to the neural retina. Development of the new lens is somewhat different than development of the normal amphibian lens. In normal amphibian lens differentiation, gamma crystalline appears first, beta crystalline appears second, and alpha crystalline appears last. When the amphibian lens is regenerated from the iris epithelium, alpha and beta crystalline appear before gamma crystalline.

The ability to regenerate the crystalline lens appears to be lost in higher vertebrates. However, lens epithelial cells of birds and mammals can be grown in culture. Confluent monolayers (primary culture of chick lens epithelium) form masses of elongated cells, called lentoid bodies. In the chick, alpha, beta, and delta crystalline, as well as the main intrinsic membrane protein (MIP 26) are produced by the cells in these lentoid bodies. However, the relative proportions of these lens proteins do not resemble those present in normal chick lenses. Long-term culture of rabbit lens epithelial cells (primary culture in conditioned medium) has led to relatively stable cell lines containing the alpha crystalline promoter. These cell lines synthesize the A and B subunits of alpha crystalline. The beta-gamrnma crystalline family is not synthesized by these rabbit epithelial cells.

Differential crystalline synthesis is observed in cultured human epithelial cells. Cultures of human fetal lens epithelial cells express both the B chain of alpha-crystalline and one of the beta-Bp. Although human cell lines maintain their epithelial cell nature when grown on haptotactic surfaces, they form lentoid bodies on non-haptotactic surfaces. These lentoid bodies express gamma-crystalline.

With the advent of endocapsular phacoemulsification and posterior chamber phacoemulsification and aspiration after anterior lens capsule removal as treatment for cataracts, spontaneous growth has been observed to occur on that portion of the lens capsule remaining in the eye following surgery. Particular embodiments of the present invention are based on the inventor's study of the spontaneous growth in the lens capsules following endocapsular phacoemulsification.

The progressive steps in the process of spontaneous regeneration of tissue of ectodermal origin have been described well for the areas of skin epidermis and corneal epithelium. Another ectodermal derivative, the crystalline lens, was reported in 1827 to regenerate in rabbits. However, research in this area has progressed more slowly. Investigators have found that the lens regenerative process is dependent on an intact anterior and posterior lens capsule. After extraction of the lens capsular contents, regenerating lens tissue first is noted two weeks postoperatively, beginning in the periphery of the capsule and occurring more rapidly in younger rabbits.

In 1842, Valentin described for the first time the regenerated rabbit lens on a microscopic level, demonstrating the presence of characteristic round or polyhedral-shaped crystalline cells (G. Valentin, "Mikroscopische Untersuchung zweier wiedererzeugter Krystallinsen des Kaninchens," *Ztschr S. Rat. Med.*, 1, 227-37 (1842)). Valentin suggested that regeneration takes place by effusion into the capsule of initially liquid cytoblastic masses, which subsequently develop into lens cells and fibers. In 1960, Stewart showed that when embryonic tissue was implanted into the capsular bag after lens evacuation, the new lens fibers were aligned in the typical concentric pattern of the mature lens. Stewart also demonstrated that lens differentiation occurred at the equator (D. S. Stewart, "Further Observations on Degenerated Crystalline Lenses in Rabbits, with Special Reference to Their Refractive Qualities," *Trans Ophthalmol Soc UK*, 80:357 (1960)).

To verify that the process develops from residual lens epithelial cells (rather than retained lens fibers), the inventor examined the histologic findings in the early post-operative period during the phase of early lens regrowth in rabbits.

Lens fiber differentiation in the embryo has been shown to involve loss of mitotic activity, marked cellular elongation, intensive synthesis of lens specific proteins called crystallines, and loss of the cell nucleus. As in embryonic development, lens regeneration proceeds by cellular proliferation along the anterior and posterior capsule (days 1-7) and is followed by elongation of the posterior epithelial cells and migration of the nuclei anteriorly (1 month). During the second month, lens differentiation occurs at the equatorial zone, with gradual elongation of cells, anterior migration of nuclei, and eventual loss of the nuclei. The mechanical forces exerted on the capsule bag may play an important role in lens fiber differentiation. The regenerative process in the New Zealand albino (NZA) rabbit after endocapsular lens extraction appears to follow the stages seen in the embryonic development of the lens (A. E. Gwon, et al., "A Histologic Study of Lens Regeneration in Aphakic Rabbits," *Investigative Ophthalmology & Visual Science*, 31(3): 540-547 (1990)).

Extracapsular cataract extraction with intraocular lens (IOL) implantation is the procedure of choice for the treatment of cataracts. The single most frequent cause of decreased visual acuity after this surgery is delayed opacification of the posterior capsule. This opacification occurs secondarily to anterior lens epithelial cell migration and myoblastic transformation, contributing to wrinkling and fibrosis of the posterior capsule and resulting in visual distortion. IOL implantation tends to delay the onset of opacification.

Previous studies have shown that lens regeneration can occur spontaneously after endocapsular phacoemulsification and irrigation/aspiration of the lens capsular contents of NZA rabbits, when the anterior and posterior capsules are left relatively intact. The inventor has demonstrated that the growth curves for lens regeneration differ with age in NZA rabbits after endocapsular phacoemulsification of the lens and irrigation/aspiration. The inventor found that lens regeneration was significantly faster in younger animals (A. Gwon et al., "Lens Regeneration in Juvenile and Adult Rabbits Measured by Image Analysis," *Investigative Ophthalmology & Visual Science*, 33(7):2279-2283 (1992)).

Lens regeneration in young animals occurred as early as 2 weeks after surgery, and the capsular bag reached maximum filling capacity with newly regenerated lens material at approximately 3 months. In comparison, lens regeneration in adult animals was not observed until 5 weeks after surgery and was still occurring as long as 6 months later. A similar pattern occurs in humans. Posterior capsule opacification after extracapsular cataract extraction with IOL implantation occurs more frequently and at a much faster rate in children than in adults.

Figure 3:
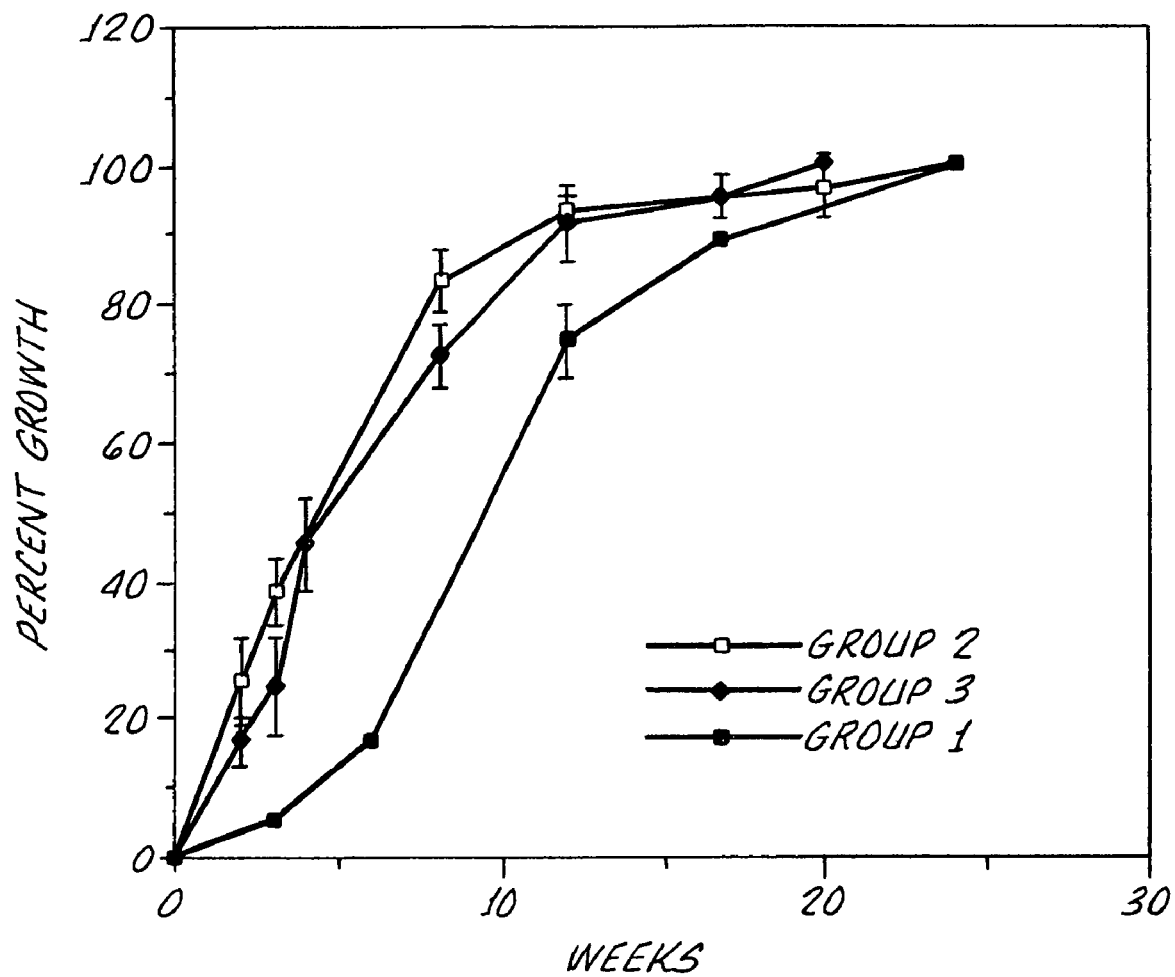
FIG. 3 depicts a digital image analysis graph of lens regrowth rates in old rabbits (Group 1), young rabbits (Group 2), and young rabbits with low vacuum of capsule bag (Group 3) in accordance with an embodiment of the present invention.

FIG. 3 depicts a digital image analysis graph of lens regrowth rates in old rabbits (Group 1), young rabbits (Group 2), and young rabbits with low vacuum of capsule bag (Group 3). As illustrated in FIG. 3, the initial lens regrowth rate in old rabbits was much slower than that of young rabbits.

The reported incidence of posterior capsule opacification (secondary cataract) varies greatly, depending upon patient age, follow-up time, and presence and type of IOL. In children, the incidence of posterior capsule opacification is nearly 100%, whereas in adults the reported incidence varies from 15% to nearly 50%, 2-3 years after surgery. Posterior capsule opacification is the product of the proliferation and migration of lens cells remaining in the capsular bag and the growth of cells of nonlenticular origin.

In another study, the inventor showed that lens regeneration was shown to occur after endocapsular extraction of posterior subcapsular cataracts induced by intravitreal injection of Concanavalin A (A. Gwon et al., "Lens Regeneration in New Zealand Albino Rabbits After Cataract Extraction," *Investigative Ophthalmology & Visual Science*, 34(6):2124-2129 (1993)). The regenerated lenses weighed less than lenses regenerated after normal lens extraction. The regenerated lenses of the cataract group were similar to the control normal lens group in transparency. The regenerated lenses are fairly translucent but because of abnormalities in the rate of regrowth in different parts of the capsule bag, these lenses are not optically clear and irregularities in structure exist. In addition, the lenses have varying degrees of vacuolization and some areas of opacification. No differences in structure and translucency of the regenerated lenses in the normal versus cataract lens group was visible by slit lamp biomicroscopy (not shown). However, the regenerated lenses were noted to be smaller.

In numerous studies, lenses that have been regenerated following endocapsular lens extraction in NZA rabbits have been irregular in shape, appearing primarily doughnut-shaped. The newly formed lenses are irregular in shape as a result of the lack of lens growth at the site of the anterior capsulotomy and its adhesion to the posterior capsule. These regenerated lenses have had variable translucency because of irregular alignment of newly formed fibers, which may partly result from irregular proliferation of cells in zones of wrinkling or folding of the lens capsule in the early post-operative period. To improve the transparency of the regenerated lenses and their therapeutic utility, investigators have attempted to mimic the embryonic environment with limited success.

It became apparent to the inventor that a suitable mechanism for sealing the anterior capsulotomy and restoring the continuity of the anterior capsule might be beneficial. Physical forces exerted on the lens may affect the rate of cell proliferation and distribution of dividing cells in this tissue. Accordingly, the inventor examined the enhancement of lens regeneration in NZA rabbits through the restoration of lens capsule integrity by sealing the anterior capsulotomy with a collagen patch and by filling the capsule bag with air, sodium hyaluronate (Healon®), or perfluoropropane gas (A. Gwon et al., "Restoring Lens Capsule Integrity Enhances Lens Regeneration in New Zealand Albino Rabbits and Cats," *J Cataract Refract Surg.*, 19: 735-746 (1993)).

The inventor attempted to seal the anterior capsulotomy with fibrin sealant, Mussel adhesive protein, and cyanoacrylate. The inventor was able to restore the lens capsule integrity by inserting a collagen patch at the time of surgery to seal the capsule and restore its continuity and thus improve the shape and structure of the regenerated lens (Example 2). The inventor then filled the capsule bag with air, sodium hyaluronate (Healon®), or perfluoropropane gas to prevent adhesions between the anterior and posterior capsules and to maintain capsule tautness and shape (Example 3).

Mayer showed that the process begins in the periphery of the capsule and progresses centrally toward the site of the anterior incision (Mayer, "Uber die reproduktion der Krystallinse," *Journal der Chirurgie und Augenheilkunde* (Berlin, von Graefe und Walther) 17:524 (1832)). Textor found that lens regeneration was dependent on an intact anterior and posterior capsule and its form depended on the lesion of the capsule and how it had cicatrized (R. L. Randolph, "The Regeneration of the Crystalline Lens: An Experimental Study," *John Hopkins Hospital Reports*, 9:237 (1900)).

Sikharulidze and Stewart demonstrated that the rate and quality of the regenerated lens could be improved and had an "optical density similar to that of the normal crystalline lens" by the insertion of cytolyzed fetal tissue (T. A. Sikharuldze, "Exchange of Crystallin Lens in Rabbits by Embryonic Skin Ectoderm," *Bull Acad Sci Georg S.S.R.*, 14:337 (1956); D. S. Stewart, "Further Observations on Degenerated Crystalline Lenses in Rabbits, with Special Reference to Their Refractive Qualities," *Trans Ophthalmol Soc UK*, 80:357 (1960)). Lens fiber differentiation occurs at the equatorial zone, and alpha, beta, and gamma crystallines are produced in proportions similar to fetal or normal lens. The various embodiments of the present invention reaffirm these past findings in the art and demonstrate that regeneration of the lens can be enhanced by restoring lens capsule integrity.

By filling the empty capsular bag with a viscoelastic (Healon®) alone, with air, or perfluoropropane gas, the inventor was able to maintain the capsule tension and prevent folding and adhesion of the capsule, resulting in a more spherical shape to the regenerated lens. Fetal wounds that heal without scar formation have an extracellular matrix that is rich in hyaluronic acid.

In the group that received Healon® alone, regrowth was inconsistent because of scarring of the anterior capsulotomy site to the posterior capsule in some cases, indicating that hyaluronic acid alone was insufficient to account for the enhanced effects noted. The regrowth was much faster and more regular in the air group, whereas the perfluoropropane gas was associated with more scarring of the anterior capsule and delayed lens regeneration because of its slow resorption time. Additionally, lens regrowth proceeded from the periphery along both anterior and posterior capsules surrounding the material filling the capsule bag, which may have caused increased pressure and enhanced cellular elongation and differentiation (A. Gwon et al., "Restoring Lens Capsule Integrity Enhances Lens Regeneration in New Zealand Albino Rabbits and Cats," *J Cataract Refract Surg.*, 19: 735-746 (1993)).

As discussed hereinabove, lens regeneration has been shown to depend on restoring lens capsule integrity. With the lens capsule as an external scaffold for the lens fibers to differentiate, the regenerated lenses have had a normal cortex but the nucleus has contained a star-shaped opacity related to the irregular growth pattern and misalignment of the earliest lens fibers.

The inventor therefore evaluated a high viscosity hyaluronic acid as an internal scaffold to synchronize proliferation in the lens capsule during lens regeneration in rabbits (Example 5). The inventor's study showed that the high viscosity hyaluronic acid provided an internal scaffold for the proliferation and differentiation of lens fibers following endocapsular lens extraction.

Moreover, this study demonstrated the beneficial effect that high viscosity hyaluronic acid compositions may have on the enhancement of lens proliferation and differentiation. Compositions of high viscosity hyaluronic acid which have a beneficial effect on lens regeneration obviate the limitations of prior art. For example, the Inventor demonstrated enhancement of lens regeneration in Examples 4 and 5. The inventor demonstrated that hyaluronic acid in the form of Restylane® or Perlane® may be used to enhance lens regeneration (Example 4).

Figure 4:
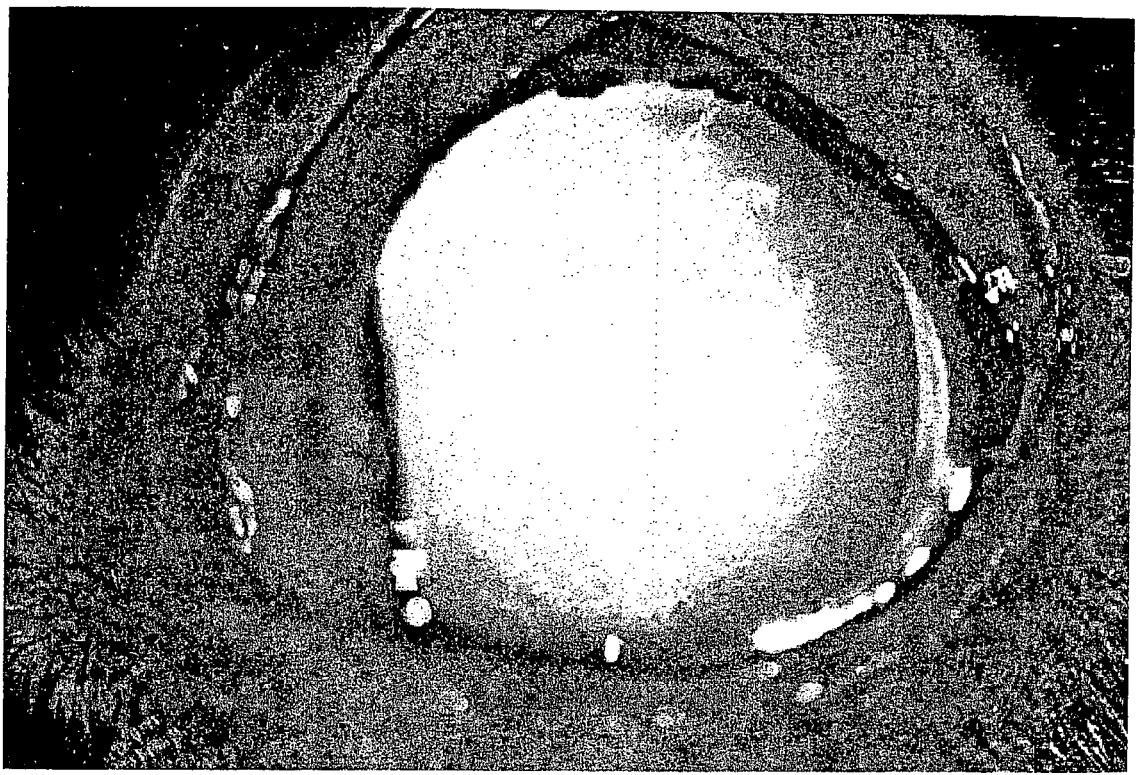
FIG. 4 depicts the honeycomb appearance of Perlane® in the lens capsule bag in accordance with an embodiment of the present invention.
Figure 5:
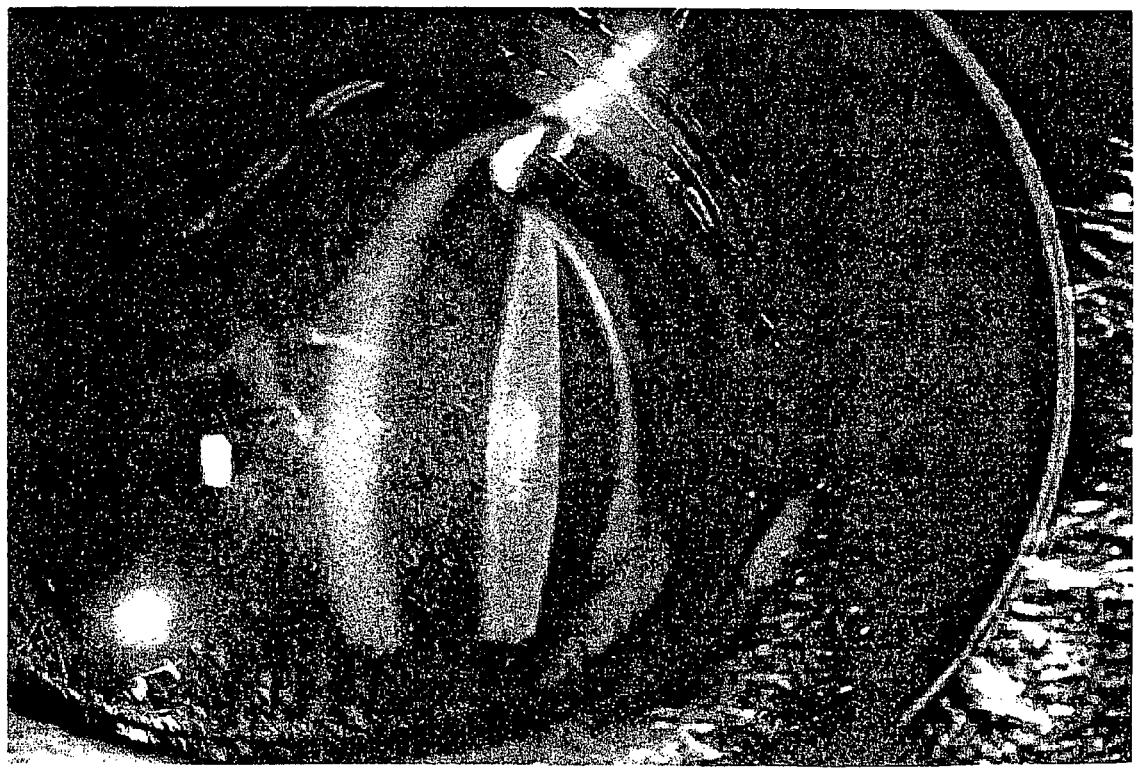
FIG. 5 depicts the clarity of the regenerated lens structure adjacent to the Perlane® in accordance with an embodiment of the present invention.
Figure 6:
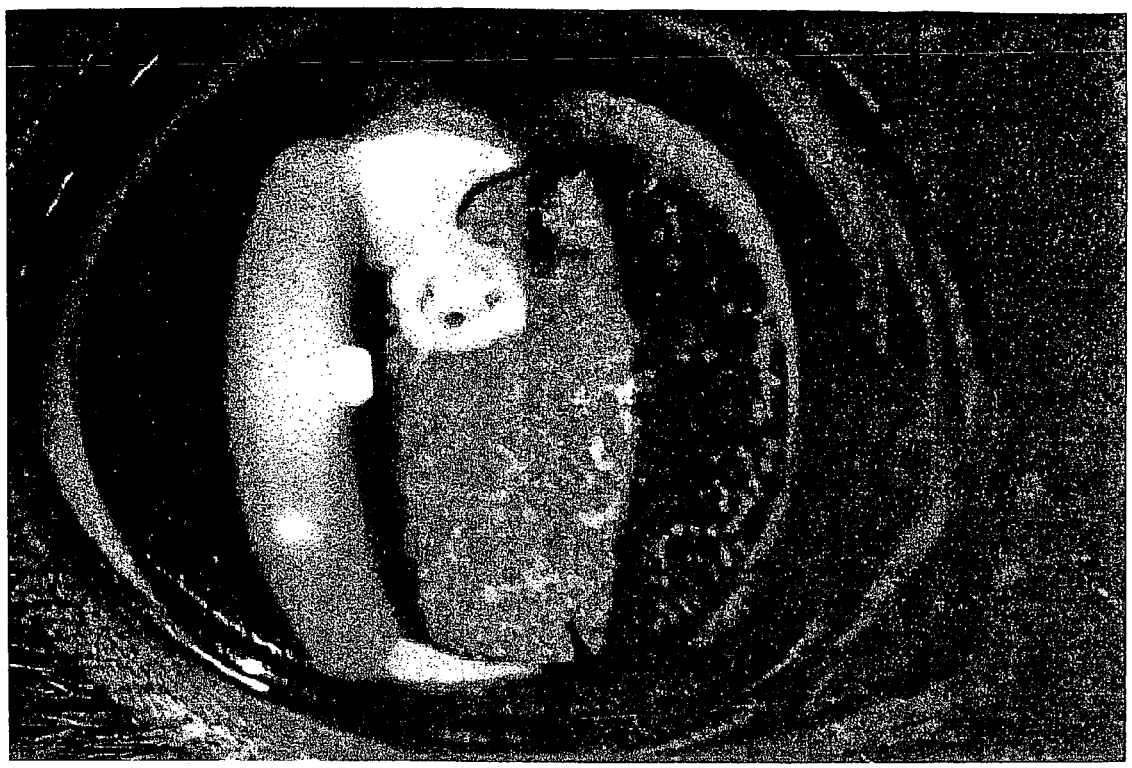
FIG. 6 depicts the honeycomb appearance of the early lens growth enhanced by Restylane® in accordance with an embodiment of the present invention.
Figure 7:
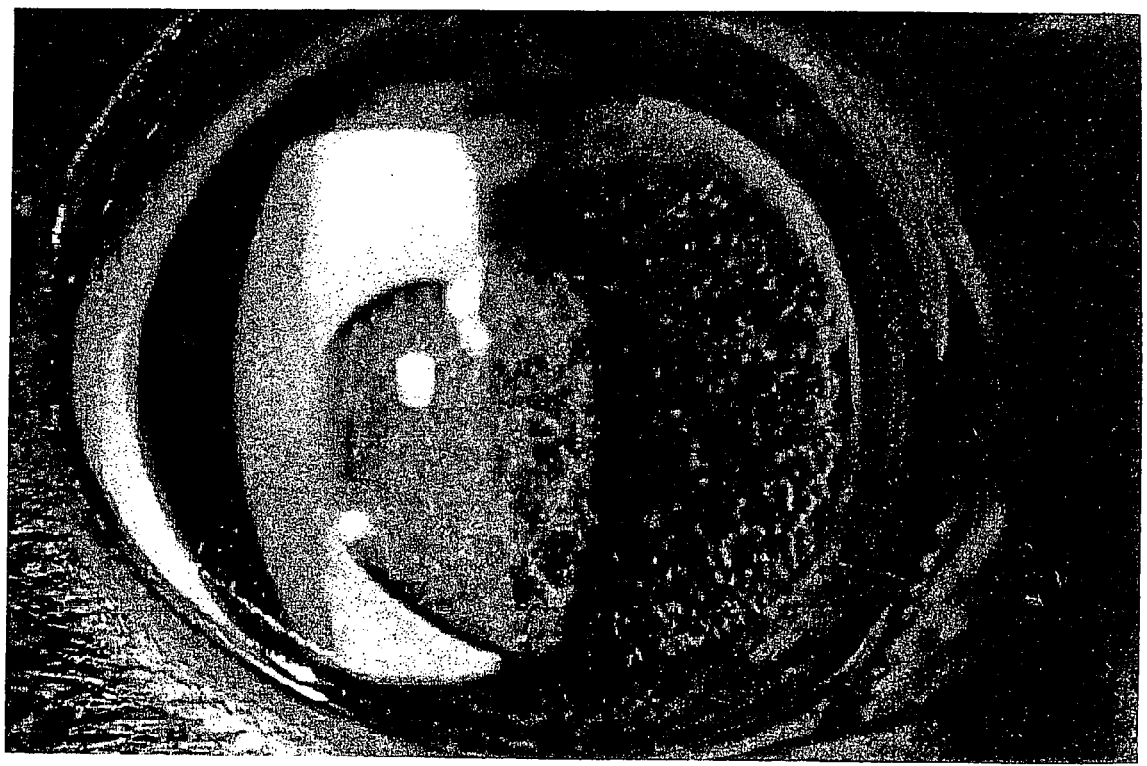
FIG. 7 depicts the honeycomb appearance of the early lens growth enhanced by Restylane® in accordance with an embodiment of the present invention.

FIG. 4 depicts the honeycomb appearance of Perlane® in the lens capsule bag, and FIG. 5 depicts the clarity of the regenerated lens structure adjacent to the Perlane® in accordance with an embodiment of the present invention. Additionally, FIGS. 6 and 7 depict the honeycomb appearance of the early lens growth enhanced by Restylane® in accordance with an embodiment of the present invention. As seen when comparing FIGS. 4 and 6, Restylane® produces a larger honeycomb pattern in the lens capsule bag than Perlane®.

In past studies, focal laser photoablation of lenticular tissue has been shown to be a relatively safe, noninvasive procedure that can be performed without lens capsule disruption (A. Gwon et al., "Focal Laser Photophacoablation of Normal and Cataractous Lenses in Rabbits: Preliminary Report," *J Cararact Refract Surg.*, 21:282-286 (1995)). In the Inventor's current study, focal photocoagulation provided limited removal of retained hyaluronic acid. The inventor's findings as discussed in Example 5 support the usefulness of an intralenticular device/therapeutic and its in vivo modification in the treatment of lenticular disorders and controlled ocular lens regeneration.

Furthermore, the inventor quantitatively analyzed the clarity of regenerated lens material after endocapsular lens extraction and restoration of the lens capsular bag with and without implantation of an intracelenticular disc lens (A. Gwon, "Intralenticular Implant Study in Pigmented Rabbits: Opacity Lensmeter Assessment," *J Cataract Refract Surg.*, 25, 268-277). The inventor sought to provide an internal scaffold for the lens epithelial cells by implanting a semipermeable synthetic lens (Example 6). The lens epithelial proliferation and differentiation did occur around the intralenticular implant, although the clarity was less than optimal. Insertion of an intralenticular disk lens into the lens capsule bag after endocapsular lens extraction was associated with poor optical quality primarily of the posterior regenerated lens tissue. While not wishing to be bound by any particular theory, it is postulated that the intralenticular lens may have blocked a factor necessary for normal metabolism of the posterior lens fibers or may have allowed the accumulation of a toxic substance behind it.

The present invention relates to the enhancement of lens regeneration though the use of hyaluronic acid and/or a collagen product in the lens capsule to improve lens cell proliferation and differentiation, as for example, to improve the configuration, shape and structure of regenerated lenses through the use of laser ablation.

In one embodiment of the present invention, a viscoelastic substance such as hyaluronic acid may be used for capsule bag filling to enhance the regeneration of lenses following phacoemulsification and irrigation/aspiration of both the natural and cataractous lens and sealing of the anterior capsule. Various quantities, molecular weights, concentrations, and/or forms of hyaluronic acid products may be used to improve the lens cell proliferation and differentiation. For example, a quantity between 0.01 to 3 cc of hyaluronic acid may be used to fill the lens capsule bag to improve the lens cell proliferation and differentiation.

In another embodiment, hyaluronic acid compound at a concentration of about 20 mg/ml in the form of Restylane®, Perlane® or similar formulations (Example 4) may be used to fill the capsule bag to enhance lens regeneration. In the range of effective concentrations, the hyaluronic acid compound will generally be in the form of a gel or similarly viscous composition. Effective concentrations of hyaluronic acid compounds may be those that will biodegrade or dissolve after two weeks postoperatively. For example, in one embodiment, an effective concentration of a hyaluronic acid compound dissolves between two to eight weeks postoperatively, as a compound with this property is believed to enhance lens regeneration.

For optimum lens regeneration to take place, the hyaluronic acid compound used to fill the capsule bag, should not biodegrade too quickly to give the hyaluronic acid compound ample time to enhance lens regeneration. The hyaluronic acid or viscous substance used in accordance with the present invention should retain the desired shape or provide a scaffold until the earliest lens fibers have measurably aligned to allow normal lens structure and suture formation. The time that the hyaluronic acid compound should remain in the capsule bag before it biodegrades depends on the age of the animal since lens regrowth rates vary with age (FIG. 3).

For example, since initial lens regrowth rate in old rabbits is slower than in young rabbits (FIG. 3), the hyaluronic acid compound used to fill the capsule bag in older rabbits would biodegrade at a slower rate than a hyaluronic acid compound used in younger rabbits. For hyaluronic acid compounds that biodegrade at slower rates, hyaluronic acid may be removed from the lens capsule bag by focal laser photocoagulation as described more fully below and by other methods known in the art.

Hyaluronic acid is used in accordance with the present invention to enhance lens regeneration by providing an internal scaffold for the proliferation and differentiation of lens cells. One skilled in the art will readily appreciate that a variety of high viscosity hyaluronic acid compositions, glycosaminoglycans (GAG's), and/or formulations thereof may be used in accordance with alternate embodiments of the present invention.

For example, suitable hyaluronic compositions may include, but are not limited to the following: Restylane®, Perlane®, a variant formulation of Healon®, and/or compositions that include high viscosity hyaluronic acid forms such as those described in U.S. Pat. Nos. 6,537,795; 6,090,596; 4,764,360; 6,086,597; 6,368,585; and 5,681,825; U.S. Patent Application Publication No. 2002/0018898 (Ser. No. 09/855,923), and in European Patent Application 0760863 B1, all of which are incorporated herein by reference in their entirety as if fully set forth.

Any variant formulation or analogous composition of any of the aforementioned hyaluronic compounds and/or GAGs including, but not limited to hyaluronic acid forms with higher or lower molecular weights, hyaluronic acid forms at variant concentrations, combinations of two or more of the abovementioned compositions, and/or combinations of any of the aforementioned hyaluronic compositions with other suitable agents may be used in accordance with alternate embodiments of the invention.

Furthermore, inventive compositions may include a hyaluronic acid compound as well as any number of conventional carriers, additives, preservatives, antibiotics, therapeutic agents and the like that are generally formulated in pharmacological compositions of this nature, as will be readily appreciated by those of skill in the art. Such additional elements may, for example, promote the safety and/or efficacy of the inventive compound.

In alternate embodiments, other media can be used individually or in combination to enhance the proliferation and differentiation of lens cells in accordance with the present invention; for instance, amniotic fluid, in vitro fertilization media, growth factors (e.g., BD MATRIGEL™ Basement Membrane Matrix and BD MATRIGEL™ Basement Membrane Matrix High Concentration), and/or other substances that can enhance or control the growth and proliferation of cells will be readily appreciated by one skilled in the art.

Still further embodiments of the present invention include methods for treating cataracts and other ocular diseases with phacoemulsification in connection with the inventive use of hyaluronic acid (i.e., filling the capsule bag with an effective amount of a viscoelastic substance, such as an inventive hyaluronic acid compound).

In another embodiment of the invention, lens regeneration is enhanced by sealing the anterior capsulotomy with one or more collagen patches. Insertion of a collagen patch may be effected during a procedure for treating ocular disease and/or correcting vision impairment, as for example, endocapsular lens extraction surgery. The lens capsule integrity is restored by inserting one or more collagen patches during endocapsular lens extraction surgery to seal the anterior capsulotomy and restore its continuity, which thereby improves the shape and structure of the regenerated lenses.

It will be appreciated by those skilled in the art that a variety of collagen patches may be used and that the sealing of the capsulotomy may occur in various regions in connection with various embodiments of the present invention. For example, a collagen patch that is composed of bovine collagen type IV or a 24-hour collagen shield (Chiron Ophthalmics) may be used in accordance with an embodiment of the present invention. Additionally, a collagen patch may be used to seal any opening in the lens capsule bag, not just the anterior capsulotomy. Furthermore, in an alternate embodiment, injectable collagen may be used as a supplement to or a replacement for the inserted collagen patch to further enhance lens regeneration.

In an additional embodiment, collagen may be used as an internal scaffold for lens fiber cell proliferation and differentiation. A variety of collagen-based products may be used, as for example, 25% or 50% suspensions of purified bovine dermis in saline with 0.3% lidocaine (available under the trade name Zyderm I® and Zyderm II® from INAMED Corporation; Santa Barbara, Calif.), monomolecular bovine collagen suspended in solution at 3.5% and 6.5% concentrations (available under the trade name Resoplast® from Rofil Medical International; Breda, Holland), human collagen preparation comprised predominantly of intact collagen fibers as well as other matrix proteins suspended in a neutral pH buffer (available under the trade name Dermalogen® from Collagenesis Corporation; Beverly, Mass.), and/or acellular human dermal graft processed from tissue bank-derived skin (available under the trade name Alloderm® from LifeCell Corporation; Palo Alto, Calif.).

The lens capsule is a basement membrane structure primarily composed of collagen type IV and glycosaminoglycans. It acts as an external scaffold for lens epithelial cell differentiation. Collagen has been shown to be advantageous for normal epithelial cell proliferation and differentiation, and it may function in the present invention as an internal scaffold for lens cell differentiation in the capsule bag.

It will be appreciated by those skilled in the art that a variety of collagen types may be used in accordance with the present invention. For example, the collagen patches and other collagen based products used in accordance with the present invention may be derived from bovine, human or synthetic sources; include type IV collagen; include a GAG-based compound or copolymer; and/or include collagen produced by amnion as described in U.S. Patent Application Publication No. 2004/0048796 (Ser. No. 10/397,867) which is incorporated by reference in its entirety as if fully set forth.

In another embodiment, lenticular tissue may be engineered using focal laser photophacocoagulation to remove excess viscoelastic substances and/or modify structure and clarity of the regenerated lens and/or bilenticular lens. As described in U.S. Pat. No. 6,322,556 and U.S. Patent Application Publication No. 2002/0103478 (Ser. No. 09/953,121), which are both incorporated herein by reference as if fully set forth, laser photophacoablation (laser photoablation) has been used to partially remove ocular tissue (e.g., lens tissue) to correct vision deficiencies and to treat other vision-impairing ocular problems without causing substantial damage to the surrounding tissue regions. In the present invention, laser photophacoablation may be used to remove retained high viscosity or viscoelastic substances in the regenerated lens in combination with the inventive use of hyaluronic acid and shape the regeneration tissue.

Suitable forms of hyaluronic acid that may be used in accordance with the present invention, as for example, Restylane® and Perlane®, may contain a crosslinked form of hyaluronic acid which is not readily resorbed by the body or lens. To assist in the removal of crosslinked hyaluronic acid in the regenerated lens, focal laser photocoagulation may be performed to remove some of the retained hyaluronic acid. For example, in one embodiment, focal laser photocoagulation may be performed with a Q-switched neodymium: YAG (Nd:Yag) laser over multiple treatment times. In an alternate embodiment, a neodymium: YLF (Nd:YLF) laser may be used in accordance with the present invention. In a further embodiment, focal laser photocoagulation may be performed with a femtosecond laser in accordance with the present invention.

In an embodiment of the invention, laser photoablation of the retained viscous material in the lens capsule bag may be performed by directing a pulsed laser beam at the viscous material with an amount of energy effective for photoablating the viscous material without causing substantial damage to the surrounding tissue region. The laser is initially directed, or focused, at a focal point below an anterior surface of the viscous material, and such focal point is moved toward the anterior surface of the viscous material in order to ablate the viscous material.

The anterior surface is in reference to the lens capsule bag in which the viscous material is retained. An alternative embodiment of the present invention includes the initiation of photoablation of the surface of the viscous material's anterior surface and thereafter moving the focal point inwardly and away from the anterior surface in order to promote the absorption of laser by products by adjacent healthy tissue. In other embodiments, a plurality of portions of the viscous material may be photoablated. Any of the foregoing variations of laser photoablation methods may be performed multiple times until the desired quantity of viscous material is removed.

Various laser types, laser characteristics, and various methods for laser photophacoablation, are described in U.S. Pat. No. 6,322,556 and U.S. Patent Application Publication No. 2002/0103478 (Ser. No. 09/953,121), both of which are incorporated by reference herein as if fully set forth, may be used in accordance with the present invention. Additionally, it will be readily appreciated by those skilled in the art that a variety of other lasers and other methods for laser photophacoablation may be used in accordance with alternates embodiments of the present invention.

The laser used in the present invention may have a variety of characteristics. For example, the laser used may have any or all of the following characteristics: an operating frequency in the visible and infrared (IR) spectrum; a repetition rate ranging from about one to about 1000 Hertz; a pulse width ranging from about 1 femtosecond to about 1 millisecond; an energy level per pulse ranging from about 1 nanojoule to about 50 millijoules; a focused spot size (diameter) between about 1 micron and about 100 microns;

a "zone of effect limited to between about 1 and about 200 microns with little collateral effect. In one embodiment, the laser may have the following characteristics: an operating frequency of about 1053 nanometers (nm); a repetition of about 1000 pulses per second; a pulse width of about 60 picoseconds; an energy level per pulse of about 60-140 microjoules, a focused spot size (diameter) of about 20 microns, and a zone of effect limited to about 50 microns.

In those embodiments of the present invention directed to methods for treating ocular disease and/or correcting vision impairment, one can use these methods to treat any disease in which enhancing lens regeneration has a beneficial effect on a patient (e.g., ameliorating a disease, lessening the severity of its complications, preventing it from manifesting, preventing it from recurring, merely preventing it from worsening, or a therapeutic effort to effect any of the aforementioned, even if such therapeutic effort is ultimately unsuccessful). Methods of the present invention may be used to treat any diseases which are affected by lens tissue loss or damage, or ocular conditions or impairments which involve a medical procedure comprising the removal or alteration of lens tissue.

EXAMPLES

The Examples described herein demonstrate various aspects of the present invention in connection with the enhancement of lens regeneration. Such uses may be particularly advantageous in treating those diseases in which regenerating lens cells has a beneficial effect. Such diseases include, for example, cataracts. However, as noted above, the present invention has uses beyond those illustrated herein, and the ensuing Examples are in no way intended to delineate the extent to which the present invention may find application in the medical arts.

Example 1

Preparation of Animals

Endocapsular lens extraction by phacoemulsification and irrigation/aspiration of the lens through a 2-3 nm capsulorhexis was performed in rabbits. Following removal of the original lens, a high viscosity hyaluronic acid was injected into the capsule bag, and a collagen patch was placed inside the capsulorhexis and brought up against the capsulotomy with an air bubble in the bag. The animals were followed postoperatively by slit lamp biomicroscopy. Following euthanasia, eyes were enucleated, paraffin embedded and H & E slides prepared for routine histology.

Example 2

Insertion of Collagen Patch in Lens Capsule

The inventor restored the lens capsule integrity by inserting a collagen patch at the time of endocapsular lens extraction surgery to seal the anterior capsulotomy and to improve the shape and structure of the regenerated lenses. Lens regeneration was first noted as early as one to two weeks following surgery. Regenerated lens filled approximately 50% of the capsule bag at two weeks and 100% by five weeks. Subsequent growth was in the anterior-posterior direction. Lens thickness increased by 0.3 mm per month. The regenerated lenses were spherical with normal cortical structure and a nuclear opacity. Restoration of lens capsular integrity with a collagen patch following endocapsular lens extraction enhanced the shape, structure, and growth rate of the regenerated lenses. In addition, lens regeneration was shown to occur in two cats.

Example 3

Filling of Capsule Bag with Air, Sodium Hyaluronate, or Perfluoropropane

After insertion of a collagen patch the inventor then filled the capsule bag with air, sodium hyaluronate (Healon®), or perfluoropropane gas to prevent adhesions between the anterior and posterior capsules and to maintain capsule tautness and shape. Lens thickness measurements at one and two months represent the filled capsule bag containing lens regrowth as well as most probably a mixture of balanced salt solution (BSS), Healon®, aqueous, and collagen degradation products and injured lens epithelial cells. From 4 to 12 months, lens thickness increased gradually but in progressively smaller increments.

The collagen patch occluded the anterior capsulotomy for up to two weeks before dissolution resulting in a linear scar at the capsulotomy site. The capsule bag was distended and maintained taut without surface wrinkles for one, five, and eight weeks in the Healon®, air, and perfluoro-propane groups, respectively.

Lens regrowth was noted as early as one, two, and three weeks in the Healon®, air, and perfluoropropane groups, respectively. Regrowth proceeded from the periphery of the capsule bag centrally along the anterior and posterior capsules, engulfing the Healon®/aqueous. Lens regrowth was more complete, and the overall shape of the lens was spherical in the air and perfluoropropane groups. With time, the earliest fibers became progressively more compacted centrally, resulting in a star-shaped nuclear opacity. In all groups, the newer cortical fibers appeared translucent and similar to normal, with the air group having the smallest nuclear opacity and the perfluoropropane group having the largest.

Example 4

Filling of Capsule Bag with Hyaluronic Acid, 20 mg/ml, in the Form of Restylane® and Perlane®

Hyaluronic acid, 20 mg/ml (in the form of Restylane® and Perlane®) was shown to enhance lens regeneration with the new lens cells differentiating in a normal configuration around the retained form of hyaluronic acid (FIGS. 5-8). The first signs of lens cell proliferation were seen as early as two weeks postoperative with full growth around the centrally retained hyaluronic acid at seven weeks. The newly formed lens had normal clarity and shape peripheral to the retained Restylane® or Perlane® in the center. While the capsule bag acted as an outer scaffold for the differentiation of lens fibers, the hyaluronic acid appeared to act as an inner scaffold for the lens fiber differentiation. Restylane® and Perlane® were shown to promote lens fiber alignment such that the innermost regenerated lens fibers, as well as the outermost cortical lens fibers formed an elliptical or spherical shaped lens.

Example 5

Evaluation of Hyaluronic Acid as an Internal Scaffold for the Proliferation and Differentiation of Lens Fibers The inventor evaluated a high viscosity hyaluronic acid as an internal scaffold to synchronize proliferation in the lens capsule during lens regeneration in rabbits. Endocapsular lens extraction of the lens through a 2-3 mm capsulorrhexis was performed in 8 eyes of 4 Dutch Belt pigmented rabbits (age 8 weeks, wt 2 kg). Healon® was injected into the capsule bag. A collagen patch was placed inside the capsulorrhexis and brought up against the capsulotomy with an air bubble in the bag. The animals were assessed postoperatively by slit lamp biomicroscopy. Following euthanasia, eyes were enucleated, parafin-embedded and H & E slides prepared. In one eye, focal laser photocoagulation was performed with an Nd:YAG laser to remove some of the retained hyaluronic acid.

In 3 eyes, the collagen patch slipped and capsulotomy closure was incomplete. In 5 eyes, lens cellular proliferation was noted at 2 weeks postop and full lens growth around the central viscoelastic mass was noted at 7 weeks. The regenerated lenses had a normal spherical shape, good clarity, and lens structure with normal fiber alignment around the residual viscoelastic material. Histology revealed normal lens structure with a monolayer of anterior lens epithelium, lens differentiation at the equatorial region, and normal lens fiber morphology. Centrally, the retained hyaluronic acid appeared as an elliptical homogenous bluish mass. In the eye treated with focal photocoagulation, partial clearing of the hyaluronic acid was noted.

High viscosity hyaluronic acid provided an internal scaffold for the proliferation and differentiation of lens fibers following endocapsular lens extraction in Dutch Belt pigmented rabbits. Focal photocoagulation provided controlled removal of retained hyaluronic acid and lens fibers. The data support the utility of an intralenticular device/therapeutic and its in vivo modification in the treatment of lenticular disorders.

Example 6

Opacity Lensmeter Assessment

The clarity of regenerated lens material was quantitatively analyzed. Endocapsular lens extraction through a 2-3 mm capsulhorrhexis was performed in New Zealand/Dutch Belt pigmented rabbits. In the test group, an Acuvue® or a Survue® disposable contact lens was intralenticularly implanted in both eyes with the aid of Healon®, and in the control group, the capsular bags of both eyes were distended with Healon® only and no artificial lens was implanted in either eye. A 24-hour collagen shield (Chiron Ophthalmics) was cut freehand to approximately 2 to 3 times the anterior capsulotomy diameter, which ranged from 2.5 to 3.5 mm after lens removal. The collagen patch was coated with Healon® and inserted into the capsule bag in both test and control eyes. Air was injected to distend the capsular bag and maintain the collagen patch behind the anterior capsulotomy. The animals were assessed postoperatively by slit lamp biomicroscopy. The Interzeag Opacity Lensmeter 701 (OLM) was used to quantify lens opacification. Following euthanasia, eyes were examined by light microscopy, parafin-embedded and H & E slides prepared, and prepared for electron microscopy examination.

Mean OLM results were similar in both groups at weeks 1, 2, 3 and 4. After one month, progressive central compaction of early irregular regenerated lens fibers was associated with increased OLM readings that were higher in the intralenticular implant group that in the control group. Regenerated lens opacification was greater in tissue posterior to the intralenticular lens than anterior to the disc lens.

In the early postoperative period, an OLM score less than 20 generally reflected the clear media before full lens regenerative tissue filled the capsular bag. As time progressed, the earliest imperfectly aligned regenerated lens fibers became progressively more compacted centrally resulting in a dense star-shaped nuclear opacity and increasing OLM score.

Figure 8A:
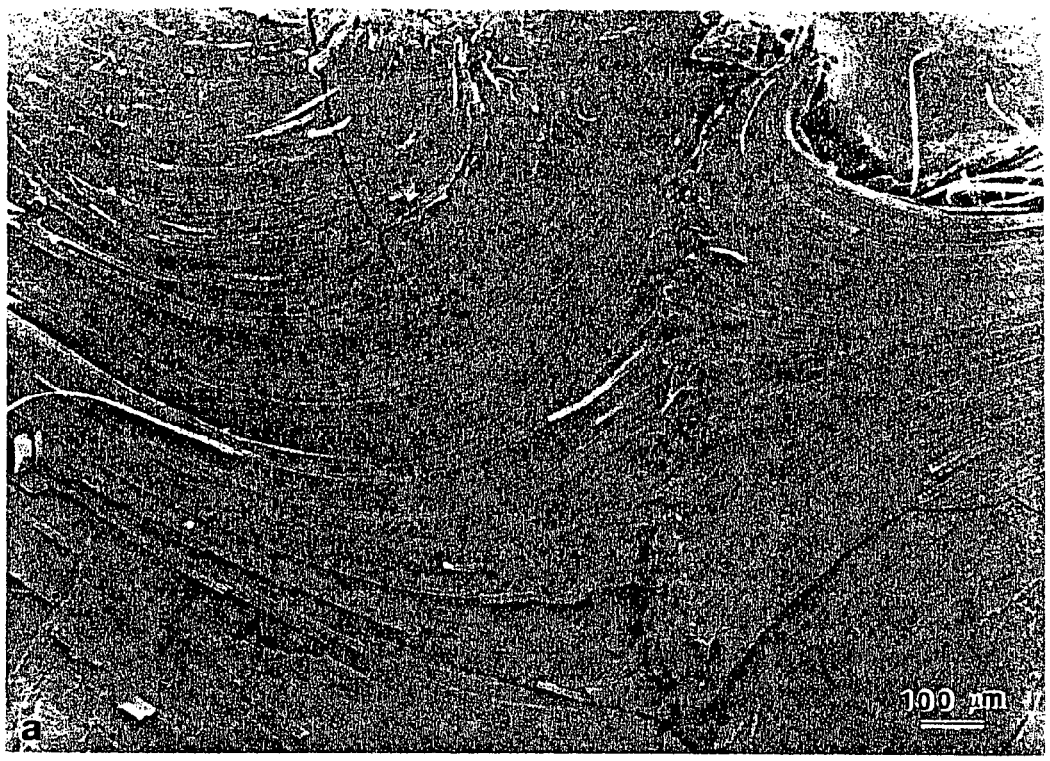
FIGS. 8A and 8B illustrate representative scanning electron micrographs of fibers formed around an intralenticular implant in accordance with an embodiment of the present invention.
Figure 8B:
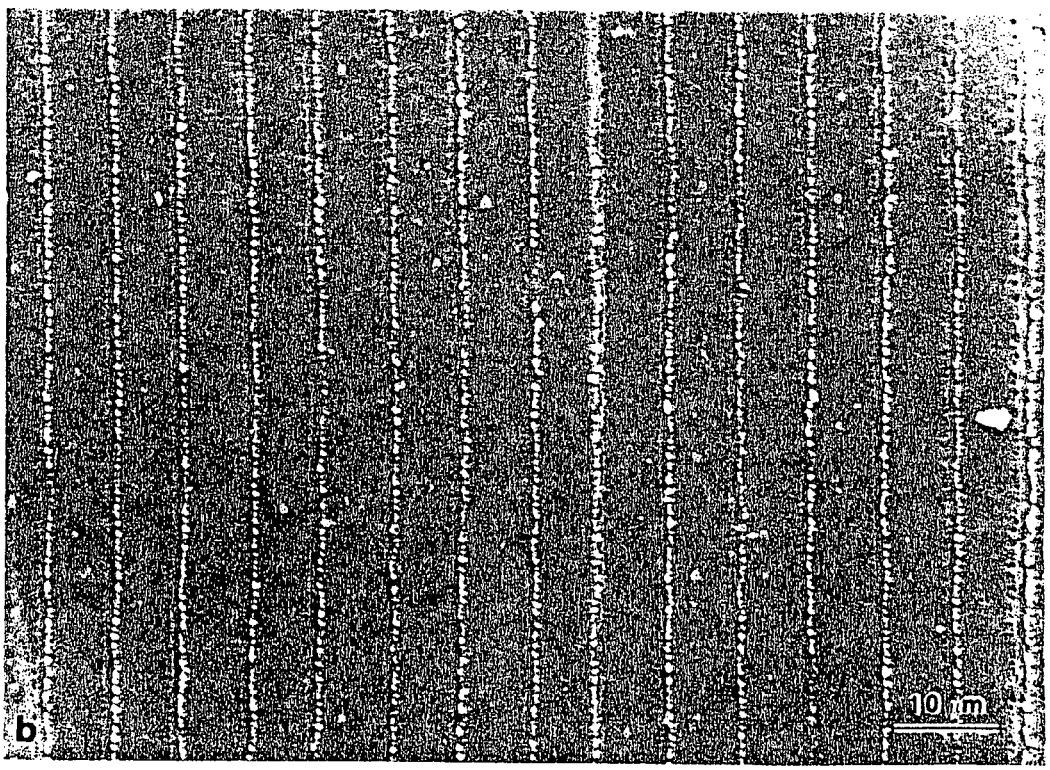

Additionally, upon gross examination, it was apparent that relatively normal (uniform size and shape) fibers grew around the intralenticular implant. However, on close scanning electron microscopic examination of fiber arrangements, fiber ends did not overlap and form normal sutures (FIG. 8A). These fibers were not grouped into quadrants. The ends of these fibers were acutely curved in varying directions. The result was the creation of swirling suture patterns with more than 2 anterior and posterior branches. Nevertheless, the fibers were clearly arranged in concentric shells and radial cell columns. In addition, fibers were uniformly hexagonal along their length and featured typical lateral interdigitations arrayed along their length (FIG. 8B).

Although there has been hereinabove described a specific method for controlled ocular lens regeneration in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A method for treating an ocular condition in a mammal, said method comprising:
   removing an original lens to leave an empty lens capsule;
   filling the empty lens capsule with a gas to maintain capsule tension and prevent folding of the empty lens capsule;
   disposing a substance into said empty lens capsule that provides and internal scaffold for proliferation and differentiation of lens fibers; and
   selectively removing said substance by laser photoablation.

2. The method according to claim 1 further comprising removing, by laser photoablation, a portion of the proliferated lens in order to control the shape and size thereof.

3. The method according to claim 1 wherein said laser photoablation further comprises:
   focusing a laser into said lens capsule with a focal point below an anterior surface of said lens capsule;
   pulsing said laser at said focal point; and
   moving said focal point towards said anterior surface of said lens capsule while pulsing said laser to ablate said at least a portion of said substance.

4. The method of claim 1, further comprising:
   inserting at least one collagen patch in said lens capsule.

5. The method of claim 1, wherein disposing a substance includes disposing a hyaluronic acid composition in the lens capsule.

6. The method of claim 1, further comprising:
injecting collagen into the lens capsule.

7. The method of claim 1, wherein said scaffold is formulated to dissolve substantially entirely after early regenerating lens fibers have formed a fairly uniform growth pattern.

8. A method for controlling the shape of regenerating lens tissue, said method comprising:
removing an original lens to leave an empty lens capsule;
filling the empty lens capsule with a gas to maintain capsule tension and preventing folding of the empty lens capsule;
disposing a substance into said empty lens capsule, said substance enabling proliferation and differentiation of lens fibers; and
selectively removing said substance by laser photoablation.

9. The method according to claim 8 further comprising removing by laser photoablation a portion of the proliferated lens fiber in order to control the shape and size thereof.

10. The method according to claim 8 wherein said laser photoablation further comprises:
focusing a laser into said lens capsule with a focal point below an anterior surface of said lens capsule;
pulsing said laser at said focal point; and
moving said focal point towards said anterior surface of said lens capsule while pulsing said laser to ablate said at least a portion of said substance.

11. The method of claim 8, further comprising:
inserting at least one collagen patch in said lens capsule.

12. The method of claim 8, wherein disposing a substance includes disposing a hyaluronic acid composition in the lens capsule.

13. The method of claim 8, further comprising:
injecting collagen into the lens capsule.

14. The method of claim 8, wherein said substance is formulated to dissolve substantially entirely after early regenerating lens fibers have formed a fairly uniform growth pattern.

* * * * *